(12) United States Patent
Hayafuji

(10) Patent No.: US 6,190,317 B1
(45) Date of Patent: Feb. 20, 2001

(54) NON-CONTACT TYPE TONOMETER

(75) Inventor: Mineki Hayafuji, Tokyo (JP)

(73) Assignee: Kabushiki Kaisha Topcon, Tokyo (JP)

( * ) Notice: Under 35 U.S.C. 154(b), the term of this patent shall be extended for 0 days.

(21) Appl. No.: 09/359,365

(22) Filed: Jul. 22, 1999

(30) Foreign Application Priority Data

Jul. 29, 1998 (JP) .................................................. 10-214061

(51) Int. Cl.⁷ ........................................................ A61B 3/16
(52) U.S. Cl. ........................................................ 600/405
(58) Field of Search ..................................... 600/398, 399, 600/401, 405; 351/205, 208, 209

(56) References Cited

U.S. PATENT DOCUMENTS

| | | | |
|---|---|---|---|
| 4,665,923 | * | 5/1987 | Kobayashi . |
| 4,995,393 | * | 2/1991 | Katsurgi et al. . |
| 5,002,056 | * | 3/1991 | Takaheshi et al. . |

FOREIGN PATENT DOCUMENTS

| | | | |
|---|---|---|---|
| 2-12086 | 3/1990 | (JP) | ................................. A61B/3/16 |
| 7-171110 | 7/1995 | (JP) | ................................. A61B/3/16 |

\* cited by examiner

*Primary Examiner*—Max Hindenburg
(74) *Attorney, Agent, or Firm*—Chapman and Cutler

(57) ABSTRACT

A non-contact type tonometer in which a stream of air is blown onto an eye to be examined by air stream blowing means, the deformation of a cornea caused by the air stream blowing means is optically detected by a cornea deformation detection optical system, and a control circuit calculates out the eye pressure of the examined eye on the basis of the result of the detection by the cornea deformation detecting optical system. Here, the quantity of the reflected light of a light beam projected onto the eye to be examined is obtained by a signal processing circuit. The above-mentioned control circuit compares with one another a plurality of light quantity data obtained by the signal processing circuit to make a judgement on whether the eye to be examined is a human eye or a model eye.

4 Claims, 3 Drawing Sheets

NON-CONTACT TYPE TONOMETER

BACKGROUND OF THE INVENTION

1. Field of the Invention

The present invention relates to a non-contact type tonometer for obtaining the eye pressure of an eye to be examined.

2. Description of the Related Art

Conventionally, a non-contact type tonometer is known in which a stream of air is blown onto an eye to be examined to deform the cornea, and the degree of the deformation thereof is optically detected to measure the eye pressure of the examined eye without contact.

In a non-contact type tonometer of this kind, its optical system is readily stained with tears, dusts, and the like, because the stream of air is blown via a nozzle to the examined eye. The stained optical system sometimes precludes the alignment thereof, or produces errors in the measurements. In order to solve this problem, Japanese Patent Gazette No. Hei 2-12086 (Prior Art 1) and Japanese Patent Laid-Open Publication No. Hei 7-171110 (Prior Art 2) disclose a non-contact type tonometer comprising a mechanism for detecting stains in the optical system and alerting thereon an examiner.

In Prior Art 1, a lens cap is mounted in front of an objective lens when the detection of the stains is performed. The stain can be detected by measuring the quantity of the reflected light from the lens cap.

However, it is very bothersome for the operator to mount the lens cap in front of the objective lens every time he or she begins detecting the stain.

Meanwhile, in Prior Art 2, a stain-detecting system detects the stain based on the quantity of the alignment detection light reflected at the cornea. The operator does not have to do anything particular in order to detect the stain, such as mounting a lens cap in front of the objective lens.

However, in the apparatus disclosed in Prior Art 2, another problem occurs when the operation check of the instrument is carried out by using a model eye. If the reflectance of the model eye is much smaller than average ones of human eyes, the stain-detecting system may judge that the stain exists, even though the optical system is not stained.

The reason is explained below.

The apparatus disclosed in Prior Art 2 judges that the stain exists, when the quantity of the cornea-reflected light of the alignment detection light becomes equal to or smaller than the prescribed value. And this "prescribed value" is determined based on the average reflectance of human eyes.

On the other hand, the reflectance of a model eye depends on its material and structure. Some model eyes have reflectance closer to the average reflectance of human eyes while others have reflectance much smaller than the average reflectance of human eyes.

Thus, when a model eye having extremely small reflectance is used, the stain alert is issued even in unstained optical systems, because the "prescribed value" is determined based on the average reflectance of human eyes.

SUMMARY OF THE INVENTION

It is an object of the present invention to provide a non-contact type tonometer which can avoid issuing the stain alert in case of measuring a model eye having smaller reflectance.

To accomplish the foregoing object, the non-contact type tonometer according to a first aspect of the present invention comprises air stream blowing means for blowing a stream of air onto an eye to be examined, cornea deformation detecting means for optically detecting a deformation of a cornea caused by said air stream blowing means, a calculation unit for calculating an eye pressure of said eye to be examined on the basis of a result of the detection by said cornea deformation detecting means, light quantity measuring means for detecting a quantity of reflected light of a light beam projected onto said eye to be examined, and judging means for judging whether said eye to be examined is a human eye or a model eye by comparing with one another a plurality of light quantity data obtained by said light quantity measuring means.

This provides an advantage that a judgement can be automatically made on whether the subject is a human eye or a model eye to prevent a stain alert displaying function from operating incorrectly.

The non-contact type tonometer according to a second aspect of the present invention is further characterized in that in the cases where the measurement on said eye pressure of said eye to be examined is conducted a plurality of times said light quantity measuring means detects the quantity of said reflected light at each measurement.

The non-contact type tonometer according to a third aspect of the present invention is further characterized in that in the cases where a difference between the plurality of light quantity data is equal to or greater than a prescribed value, the judging means makes a judgement that the eye to be examined is a human eye.

The non-contact type tonometer according to a third aspect of the present invention is further characterized in that said light quantity measuring means also serve as an alignment detecting system for detecting a state of alignment between said eye to be examined and the apparatus itself.

BRIEF DESCRIPTION OF THE DRAWINGS

The above and other objects, features and advantages of the present invention will become more apparent from the following description taken in connection with the accompanying drawings, in which.

DESCRIPTION OF THE PREFERRED EMBODIMENT

Next, an embodiment of the non-contact type tonometer according to the present invention will be described on the basis of the drawings.

[Optical System]

Figure 1A:
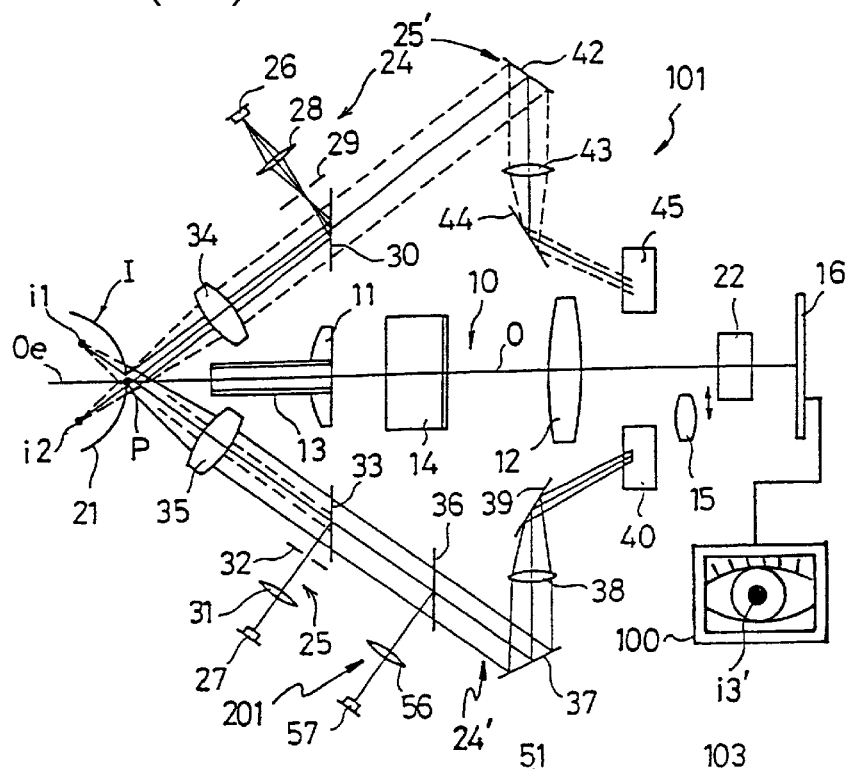
FIG. 1(A) is a plan view showing the optical system of an embodiment of a non-contact type tonometer according to the present invention.
Figure 1B:
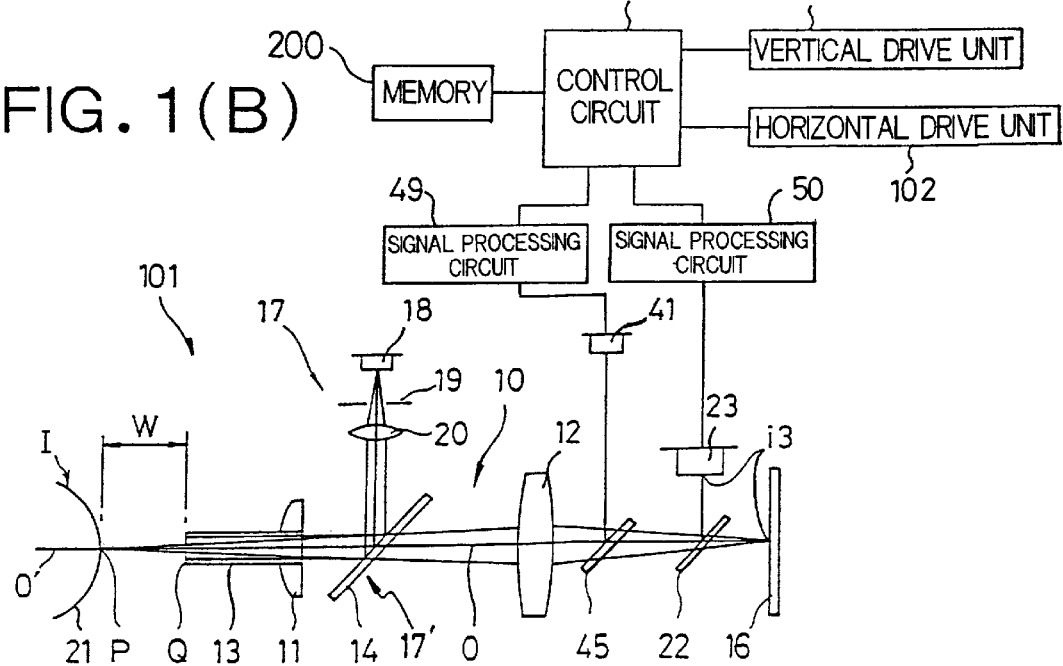
FIG. 1(B) is an explanatory diagram showing the relation between the optical system, in which the interior of the blowing nozzle of the non-contact type tonometer shown in FIG. 1(A) is used as an optical path, and a control circuit.

FIGS. 1(A) and 1(B) show the optical system of a non-contact type tonometer as the embodiment of the present invention; of these, FIG. 1(A) shows its plan view, and FIG. 1(B) its side view. Hereinafter, the vertical and horizontal directions seen from the optical system side toward an eye I to be examined are referred to as Y and X directions, respectively, and a parallel direction to the optical axis 0 of the optical system is referred to as a Z direction.

The optical system in the non-contact type tonometer of the present invention is generally composed of an anterior segment observing optical system 10, an XY alignment index projecting optical system 17, an XY alignment light receiving optical system 17', Z alignment index projecting optical systems 24, 25, Z alignment light receiving optical systems 24', 25'.

[Anterior Segment Observing Optical System]

The anterior segment observing optical system 10 comprises an objective lens 11, a half mirror 14, an imaging lens 12, a correcting lens 15, a half mirror 22, and CCD 16. A light beam to form an image of the anterior segment is transmitted through the objective lens 11, the half mirror 14, the imaging lens 12, the correcting lens 15, and the half mirror 22 to make the image on the CCD 16. The CCD 16 converts the received anterior segment image forming light into image signals, and forms the image of the anterior segment on a monitor 100.

The correcting lens 15 is to be inserted to the optical axis O when an eye I to be examined is located farther than an appropriate distance, and to be removed from the optical axis O in the cases where an eye I is located at the appropriate distance or nearer than the appropriate distance. The insertion and removal of the correcting lens 15 is carried out by a solenoid, which is not shown in the drawings. Besides, on the optical axis O of the objective lens 11 is provided a blowing nozzle 13 which blows air pulses for measuring eye pressure against an eye I.

[Alignment Detecting Optical System]

The XY alignment index projecting optical system 17 is to project onto an eye I an index for detecting the alignment of an optical axis O of the eye I with the optical axis O of the anterior segment observing optical system 10, and comprises an LED 18 as a light source for emitting infrared light, a pinhole 19 for converting a light beam from the LED 18 into point-source light, a collimating lens 20 for converting the light beam from the pinhole 19 into a collimated light beam, the half mirror 14. In other words, the optical system 17 is constituted so that the collimated light beam can be projected through the hollow of the nozzle 13 onto the cornea 21 of the eye I to be utilized as alignment index light.

The XY alignment light receiving optical system 17' is to detect the state of alignment between the optical axis O of the eye I and the optical axis O by receiving with a light receiving element the alignment index light reflected at the cornea, and comprises the half mirror 14, the imaging lens 12, the half mirror 22, a light receiving element 23 capable of detecting a two-dimensional position, and the CCD 16. More specifically, it is constituted so that the cornea-reflected light of the alignment index light is introduced through the hollow of the blowing nozzle 13, the imaging lens 12, and the like, and reflected from the half mirror 22 before being projected onto the light receiving element 23 to make an index image i3. Here, based on the imaging position of the index image i3, the state of alignment between the apparatus and the eye I is detected.

A part of the light which is not reflected by the half mirror 22 is projected onto the CCD 16 to form the index image i3 on the CCD 16. Thereby, on the monitor 100 are formed the image of the anterior segment and the index image i3'; and, based on the positional relation of these images, an examiner can confirm the state of alignment with his or her naked eye. Besides, on the monitor 100 is displayed an electrically-composed reticle image to be used as a rough standard for alignment adjustment.

The Z alignment index projecting optical system 24 comprises an LED 26 for emitting infrared light of 760 nm in wavelength, a condenser lens 28, a pinhole 29, a dichroic mirror 30 for reflecting infrared light of 760 nm in wavelength and allowing infrared light of 860 nm in wavelength to pass therethrough, and an objective lens 34 having its focus position accorded with the position of the pinhole 29, thereby a collimated light beam as an index for Z alignment being projected onto an eye I from a right oblique direction to form an index image i1 at the eye I. Meanwhile, the Z alignment index projecting optical system 25 comprises an LED 27 for emitting infrared light of 860 nm in wavelength, a condenser lens 31, a pinhole 32, a dichroic mirror 33 for reflecting infrared light of 860 nm in wavelength and allowing infrared light of 760 nm in wavelength to pass therethrough, and an objective lens 35 having its focus position accorded with the position of the pinhole 32, thereby a collimated light beam as an index for Z alignment being projected onto an eye I from a left oblique direction to form an index image i2 at the eye I. Here, as shown in FIG. 1(A), the Z alignment index projecting optical systems 24 and 25 are symmetrically arranged with respect to the optical axis O of the objective lens 11 in the anterior segment observing optical system 10.

The Z alignment light receiving optical system 25' comprises the objective lens 34, a mirror 42, a relay lens 43, a mirror 44, a total reflection mirror 45, and a light receiving element 41. As apparently seen from FIG. 1 (A), the Z alignment receiving optical system 25' shares the objective lens 34 with the Z alignment index projecting optical system 24. Accordingly, an index light beam from the Z alignment index projecting optical system 25 reflected O by the cornea is let through the objective lens 34 and the relay lens 43 to reach the total reflection mirror 45, thereby newly forming the index image i2 on the light receiving element 41.

The Z alignment light receiving optical system 24' comprises the objective lens 35, the dichroic mirror 33, a mirror 37, a relay lens 38, a mirror 39, and a total reflection mirror 40. As apparently seen from FIG. 1(A), the Z alignment light receiving optical system 24' shares the objective lens 35 with the Z alignment index projecting optical system 25. Accordingly, an index light beam from the Z alignment index projecting optical system 24 reflected by the cornea is let through the objective lens 35 and the relay lens 38 to reach the total reflection mirror 40, thereby newly forming the index image i1 on the light receiving element 41.

The index images i1 and i2 are coincidentally focused into an image on the light receiving element 41 when the distance between the top of the cornea P of the eye I and the tip Q of the nozzle is the proper operation distance, and separately imaged in the other cases. Therefore, by detecting whether or not the index image i1 and i2 are coincident, it can be judged whether or not the adjustment of the distance, i.e., Z alignment is properly done. The LEDs 26, 27 may be provided to differ in period of flashing from each other or the pinholes 29, 32 be provided to have different shapes from each other to make the judgement whether an operation distance is long or short.

Thus, in the present embodiment, the Z alignment indexes are projected from two different symmetrical directions as mentioned above as well as the two index images on the light receiving element are calculated for the positions of their centers of gravity (in other words, averaged) so that the positions of the index images are obtained from the positions of the centers of gravity. This accordingly offers an advantage of reducing measurement errors of the Z alignment even in the cases where the XY alignment is great in deviation.

[Cornea Deformation Detecting Optical System]

A cornea deformation detecting optical system (cornea deformation detecting means) 201 comprises the objective lens 35, a half mirror 36, a condenser lens 56, and a light receiving element 57, sharing a part of the optical system with the Z alignment light receiving optical system 24'. Thereby, the index light from the Z alignment index projecting optical system 24 is projected onto the light receiving element 57 via these optical elements. Quantity of the light received on the light receiving element 57 changes resulting from air pulses blown from the blowing nozzle 13 onto the cornea of the eye I. The internal pressure of the eye I is calculated based on the temporal change of the light quantity. In other words, the Z alignment index projecting optical system 24 is used also as an optical system for projecting a light beam for detecting the deformation of cornea onto the eye I.

[Calculation Control System and Drive Unit]

The non-contact type tonometer of the present embodiment further comprises: a calculation control system for making a judgement for a model eye or a human eye, and for calculating the amount of misalignment based on the output of the aforesaid alignment detecting optical system; and a drive control unit for driving and controlling the apparatus itself based on the calculations.

The calculation control system comprises a signal processing circuit 49, a signal processing circuit (light quantity measuring means) 50, and a control circuit (judging means) 51. The signal processing circuit 49 is connected to the light receiving element 41 so as to receive the output of the light receiving element 41 through an input terminal thereof, and has a function of detecting the centers of gravity of the pair of index images i1 and i2. Meanwhile, the signal processing circuit 50 is connected to the light receiving element 23 so as to receive the output of the light receiving element 23 through an input terminal thereof, and has a function of detecting the position of the center of gravity of the index image i3. As light quantity measuring means, the signal processing circuit 50 also has a function of detecting the quantity of light received by the light receiving element 23.

These detection results are then input to the control circuit 51. The control circuit 51 calculates the distance between the centers of gravity of the pair of index images i1 and i2, and the position of the center of gravity of the index image i3. The control circuit 51 also let the memory 200 store the quantity of light received by the light receiving element 23 at each measurement.

Besides, the control circuit 51 compares a plurality of light quantity levels of the received lights (light quantity data) stored in the memory 200 with one another. Here, the comparison may be made on the maximum and minimum values among the plurality of light quantity data, or on the two latest light quantity data. When the difference in the comparison is equal to or smaller than a prescribed value TH, the control circuit 51 judges that the examined eye is a model eye; and when the difference is greater than the prescribed value, the examined eye is judged to be a human eye.

The reason for the judgment described above is explained as follows.

Figure 3:
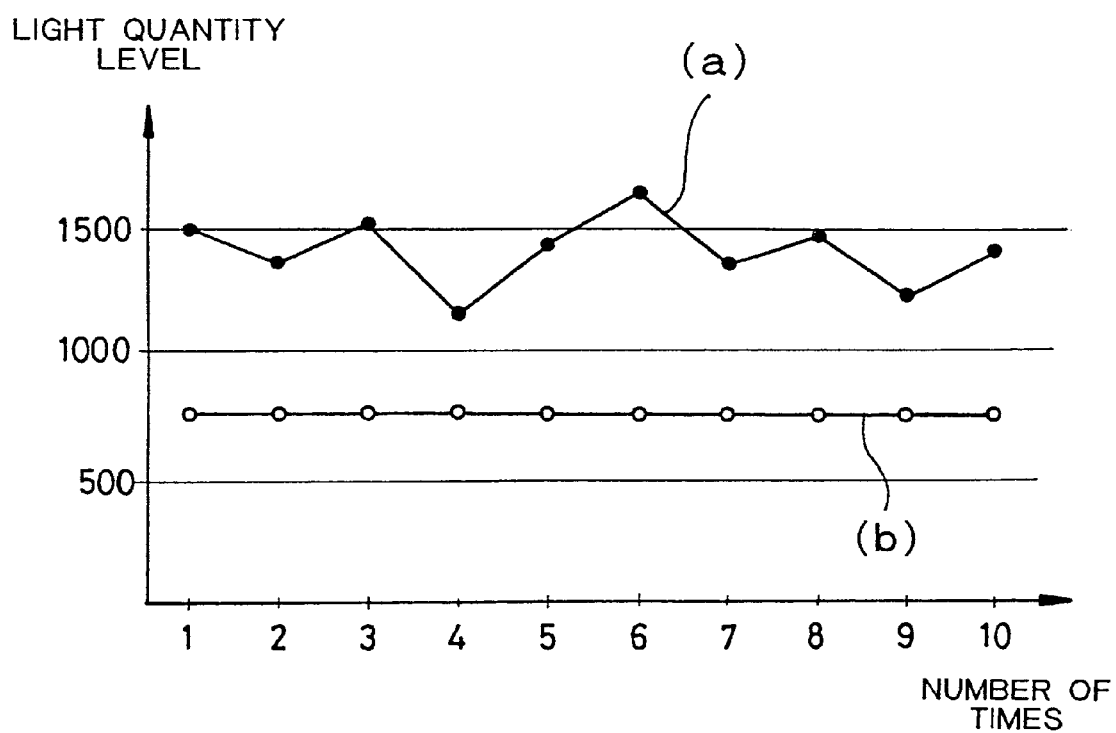
FIG. 3 is a graph showing the light quantity levels of a human eye and a model eye.

In case of human eyes, the light quantity level at the light receiving element 23 greatly changes measurement by measurement (as shown by (a) in FIG. 3), due to the fact that tears may be scattered and eyelashes may get into the optical path each time the stream of air is blown from the blowing nozzle 13 for eye-pressure measurement. On the contrary, in the cases of model eyes, no tears are scattered and no eyelash gets into the optical path even though the stream of air is blown from the blowing nozzle 13. Thus, the light quantity levels at the light receiving element 23 at each measurement are almost uniform, as shown by (b) in FIG. 3. Accordingly, properly setting the threshold value TH in the difference between light quantity levels of the received lights allows the judgement on whether a subject is a human eye or a model eye.

Having made a human-eye judgement, the control circuit 51 detects stains on the optical system from the respective light quantity levels of the received lights stored in the memory 200. On detecting stains, the control circuit 51 displays an alert on the monitor 100 and prohibits the measuring operation.

The control circuit 51 has a function of calculating the distance between the cornea of an eye I and the apparatus and the amount of misalignment Δ between the optical axis O and the optical axis of the cornea of the eye I, on the basis of the position of the center of gravity of the index image i3 and the distance between the gravity-centers of the pair of index images i1 and i2, respectively. These calculations are output to a vertical drive unit 103 and a horizontal drive unit 102. The vertical drive unit 103 and the horizontal drive unit 102 have functions of adjusting the alignment by moving an undermentioned optical measuring unit in up-and-down, right-and-left, and back-and-forth directions according to the calculations.

Besides, the control circuit 51 is constituted to send a measurement start signal for giving an instruction of starting the measurement to the optical measuring unit in predetermined cases.

[Whole Constitution]

Next, with reference to FIG. 2, description will be given of the whole constitution of the non-contact type tonometer including the concrete constitution of the vertical drive unit 103 and the horizontal drive unit 102.

Figure 2:
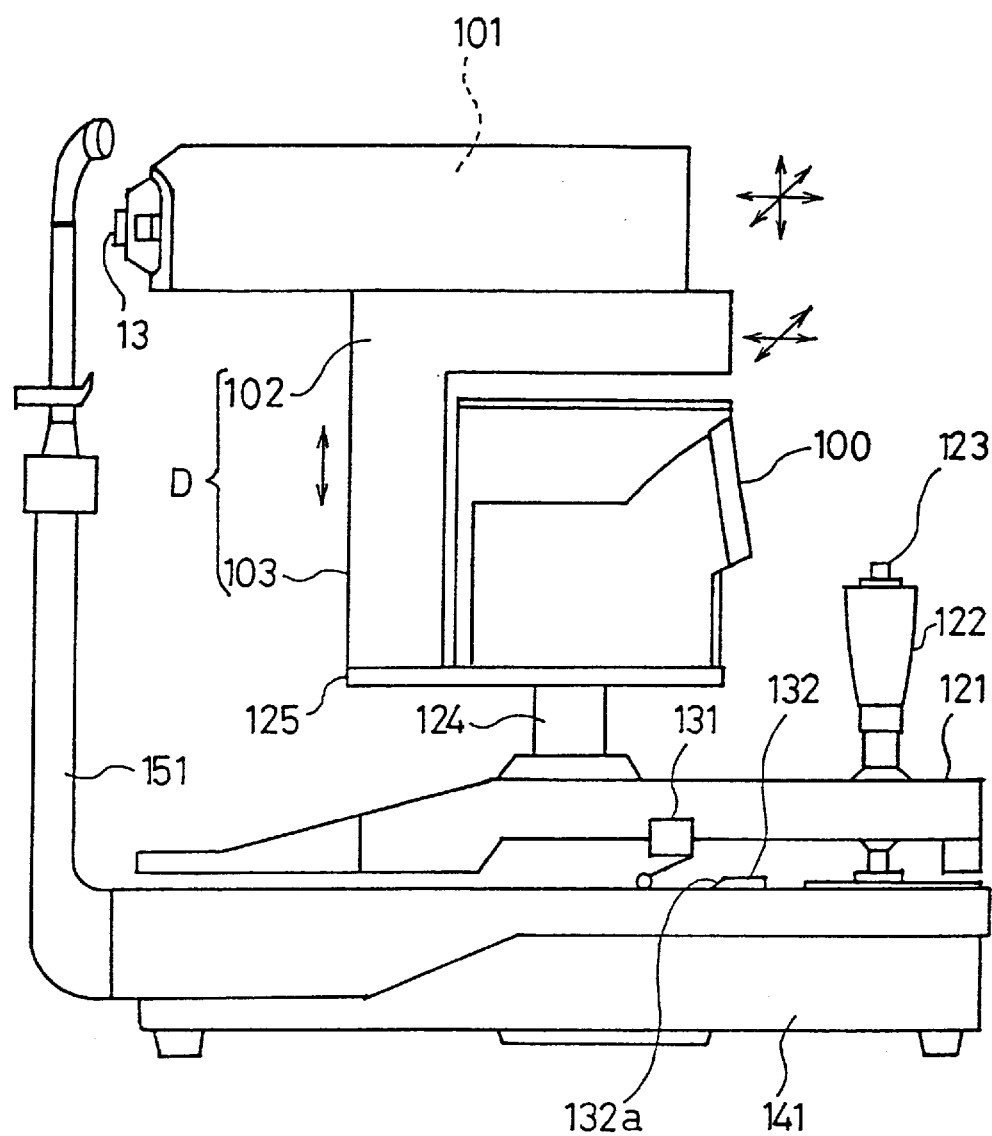
FIG. 2 is a side view of the non-contact type tonometer shown in FIGS. 1(A) and 1(B)

In FIG. 2, designated by 141 is a base having a power source built-in. On the base 141 is mounted a cradle 121 so as to move back-and-forth and right-and-left freely, and on a rear portion of the cradle 121 is supported a joy stick 122 so as to be tilted freely in any direction. The cradle 121 is constituted to move back-and-forth and right-and-left over the base 141 in accordance with the tilting operation of the joy stick 122 in back-and-forth and right-and-left directions. Since this structure is widely-known, detailed description thereto will be omitted. On an upper end of the joy stick 122 is mounted a manual measurement switch 123. The manual measurement switch 123 is used to start measurement under a manual measurement mode, description of which will be omitted.

On an upper surface of the above-described base 141 is mounted a cam plate 132 having a slanted surface 132a in its front end section, and on a side section of the cradle 121 is attached a microswitch 131. The microswitch 131 is constituted to be turned on by the cam plate 132 in moving the cradle 121 backward, so that the above-mentioned solenoid (not shown) for inserting/removing the correcting lens 15 is driven to insert the correcting lens to the optical axis O. A monitor mounting plate 125 is mounted on the center of the cradle 121 via a leg 124, and the monitor 100 is mounted on the monitor mounting plate 125.

Besides, an optical measuring unit 101 containing the optical system shown in FIG. 1 is attached onto the front end side of the monitor mounting plate 125 via a three-dimensional drive mechanism D (drive means) consisting of the above-described vertical drive unit 103 and horizontal drive unit 102 so as to allow its automatic drive in the x, y, and z directions.

[Operation]

Next, description will be given of the operation of the above-described non-contact type tonometer.

In the cases of checking the machine in its operation by using a model eye, first, the examiner is to set the cradle 121 back in advance. Here, the microswitch 131 is turned on by the plate 132 on the base 141 to insert the correcting lens 15 to the optical axis O.

Then, the examiner pushes the joy stick 122 forward to move the cradle 121 ahead, turning the microswitch 131 off to withdraw the correcting lens 15 from the optical axis O. Then, based on the image of the model eye and the reticle image displayed on the monitor 100, the examiner manipulates the joy stick 122 until rough alignment between the optical measuring unit 101 and the eye I is completed. On the completion of the rough alignment, the lights from the respective LEDs 18, 26, and 27 reflected by the cornea of the model eye enter the light receiving element 23 and the light receiving element 41. The outputs of the light receiving element 23 and the light receiving element 41 are input to the control circuit 51 via the signal processing circuits 49 and 50, respectively.

The control circuit 51 sends signals to a motor 104 in the vertical drive unit 103 and motors 108, 112 in the horizontal drive unit 102 to move the optical measuring unit 101 for the alignment. On the completion of the alignment, the signal processing circuit 50 detects the quantity of received light from the index image i3 at the light receiving element 23, and the control circuit 51 stores the quantity of received light into the memory 200 in sequence.

On the completion of the alignment, the control circuit 51 also sends out the measurement start signal to a compressed air generating unit, which is not shown in the drawings. On receiving the signal, the compressed air generating unit blows a stream of air through the nozzle 13 onto the model eye. This deforms the model eye, thereby causing a variation in the quantity of light of the light beam entering the light receiving element 57 in the cornea deformation detecting optical system 201. Based on the temporal variations in the quantity of light, the eye pressure of the model eye is calculated by a known method.

The measurement is repeated several times so that the quantity of received light of the index image i3 at the light receiving element 23 at each measurement is stored in the memory 200, and the control circuit 51 compares the light quantity levels of the received lights stored in the memory 200 to obtain the difference therebetween. In this case, since the subject is a model eye, little difference consists in the light quantity levels of the received lights. Therefore, the difference is equal to or below the prescribed value TH, so that the control circuit 51 judges that the subject is a model eye.

In the cases of the model-eye judgement, the control circuit 51 does not judge that the optical system is stained even when the lights received by the light receiving element 23 are low in quantity of light. Accordingly, the stain alert is not displayed.

On the other hand, when the measurements are made on a human eye, the light quantity levels of the received lights stored in the memory 200 exhibit great variations, so that the difference therebetween becomes large. On this basis, the control circuit 51 judges that the measuring object is a human eye. In this case, the optical system is detected for stains based on the light quantity data obtained in the plurality of measurements, like conventional cases.

In the aforementioned embodiment, the quantity of received light at the light receiving element 23 is detected in advance of the air-stream blowing after the completion of the alignment. However, the detection on the quantity of received light is not limited thereto, but may be conducted after the completion of the rough alignment or immediately after the termination of the measurements. Besides, correction may be made on the data of the quantity of received light based on the amount of misalignment Δ. Moreover, the optical system may be detected for stains based on the quantity of the light received by the light receiving element 57 for applanometry detection.

Although the invention has been described in its preferred form with a certain degree of particularity, obviously many changes and variations are possible therein. It is therefore to be understood that the present invention may be practiced otherwise than as specifically described herein without departing from the scope and spirit thereof.

What is claimed is:

1. A non-contact type tonometer comprising:

air stream blowing means for blowing a stream of air onto an eye to be examined;

cornea deformation detecting means for optically detecting a deformation of a cornea caused by said air stream blowing means;

a calculation unit for calculating an eye pressure of said eye to be examined on the basis of a result of the detection by said cornea deformation detecting means;

light quantity measuring means for detecting a quantity of reflected light of a light beam projected onto said eye to be examined; and judging means for judging whether said eye to be examined is a human eye or a model eye by comparing with one another a plurality of light quantity data obtained by said light quantity measuring means.

2. The non-contact type tonometer according to claim 1, wherein, in the cases where the measurement on said eye pressure of said eye to be examined is conducted a plurality of times, said light quantity measuring means detect the quantity of said reflected light at each measurement.

3. The non-contact type tonometer according to claim 1, wherein, in the cases where a difference between said plurality of light quantity data is equal to or greater than a prescribed value, said judging means make a judgement that said eye to be examined is said human eye.

4. The non-contact type tonometer according to claim 1, wherein said light quantity measuring means also serve as an alignment detecting system for detecting a state of alignment between said eye to be examined and the apparatus itself.

* * * * *